United States Patent
Amthor et al.

(10) Patent No.: US 10,132,897 B2
(45) Date of Patent: Nov. 20, 2018

(54) CORRECTING THE MAGNETIC FIELD OF A MEDICAL APPARATUS WITH A GANTRY

(71) Applicant: KONINKLIJKE PHILIPS N.V., Eindhoven (NL)

(72) Inventors: Thomas Erik Amthor, Hamburg (DE); Johannes Adrianus Overweg, Uelzen (DE)

(73) Assignee: KONINKLIJKE PHILIPS N.V., Eindhoven (NL)

(*) Notice: Subject to any disclaimer, the term of this patent is extended or adjusted under 35 U.S.C. 154(b) by 0 days.

(21) Appl. No.: 15/599,776

(22) Filed: May 19, 2017

(65) Prior Publication Data
US 2018/0003789 A1 Jan. 4, 2018

Related U.S. Application Data (63) Continuation of application No. 14/118,910, filed as application No. PCT/IB2012/052752 on May 31, 2012, now Pat. No. 9,664,763.

(30) Foreign Application Priority Data

May 31, 2011 (EP) .................................. 11168183

(51) Int. Cl.
*G01V 3/00* (2006.01)
*G01R 33/56* (2006.01)
(Continued)

(52) U.S. Cl.
CPC ........... *G01R 33/56* (2013.01); *A61N 5/1049* (2013.01); *G01R 33/4808* (2013.01);
(Continued)

(58) Field of Classification Search
CPC .............. G01R 33/543; G01R 33/5659; G01R 33/3415; G01R 33/36; A61B 5/055
See application file for complete search history.

(56) References Cited

U.S. PATENT DOCUMENTS 5,313,164 A * 5/1994 Starewicz ............. G01R 33/24
324/318
5,773,976 A 6/1998 Sakakura et al.
(Continued)

FOREIGN PATENT DOCUMENTS

JP 62242399 A 10/1987
JP 03151936 A 6/1991
(Continued)

OTHER PUBLICATIONS

Lagendijk, Jan J.W. et al "MRI/LINAC Integration" Radiotherapy and Oncology, vol. 86, No. 1, 2008 p. 25-29.
(Continued)

*Primary Examiner* — Walter L Lindsay, Jr.
*Assistant Examiner* — Frederick Wenderoth (57) ABSTRACT

A magnetic resonance imaging system (302) includes a magnet (306) for generating the magnetic field within an imaging zone 318. The magnet generates a magnetic field with a zero crossing (346, 404) outside of the imaging zone. The medical apparatus further includes a gantry (332) configured for rotating a ferromagnetic component (336, 510) about a rotational axis (333). A magnetic correcting element (348, 900, 1000) is located on a radial path (344, 504) perpendicular to the rotational axis. The magnetic correcting element is positioned on the radial path such that change in the magnetic field within the imaging zone due to the ferromagnetic component is reduced.

19 Claims, 8 Drawing Sheets

(51) Int. Cl.
  *G01R 33/48* (2006.01)
  *A61N 5/10* (2006.01)
  *G01R 33/3873* (2006.01)
  *G01R 33/3875* (2006.01)

(52) U.S. Cl.
  CPC .. *A61N 2005/1055* (2013.01); *G01R 33/3873* (2013.01); *G01R 33/3875* (2013.01); *H05K 999/99* (2013.01)

(56) References Cited

U.S. PATENT DOCUMENTS

| | | | |
|---|---|---|---|
| 6,198,957 | B1 | 3/2001 | Green |
| 2007/0206555 | A1 | 9/2007 | Kruspe |
| 2008/0208036 | A1* | 8/2008 | Amies ................ A61N 5/1049 600/411 |
| 2009/0149735 | A1 | 6/2009 | Fallone et al. |
| 2010/0013473 | A1* | 1/2010 | Blumich ............. G01R 33/383 324/307 |
| 2010/0013474 | A1* | 1/2010 | Casanova ............ G01R 33/383 324/307 |
| 2010/0239066 | A1 | 9/2010 | Fahrig |
| 2011/0001593 | A1 | 1/2011 | Nagata |
| 2011/0237859 | A1 | 9/2011 | Kuhn et al. |

FOREIGN PATENT DOCUMENTS

| | | | |
|---|---|---|---|
| JP | 2008220923 A | | 9/2008 |
| WO | 2004024235 A1 | | 3/2004 |
| WO | WO2004024235 | * | 3/2004 ............. A61N 5/10 |
| WO | 2007045076 A1 | | 4/2007 |

OTHER PUBLICATIONS

St Aubin J. et al "Magnetic Decoupling of the LINAC in a Low Field Biplanar LINAC-MR System" Medical Physics vol. 37, No. 9, Sep. 2010, p. 475-4761.

* cited by examiner

CORRECTING THE MAGNETIC FIELD OF A MEDICAL APPARATUS WITH A GANTRY

CROSS-REFERENCE TO PRIOR APPLICATIONS

This application claims the benefit or priority of the following applications: wherein this application is a continuation of U.S. patent application Ser. No. 14/118,910, filed Nov. 20, 2013, which is the National Stage of International Application No. PCT/IB2012/052752, filed May 31, 2012, which claims the priority of foreign application EP 11168183.9 filed May 31, 2011, all of which are incorporated herein in whole by reference.

TECHNICAL FIELD

The invention relates to magnetic resonance imaging, in particular to radiation therapy guided by magnetic resonance imaging.

BACKGROUND OF THE INVENTION

A static magnetic field is used by Magnetic Resonance Imaging (MRI) scanners to align the nuclear spins of atoms as part of the procedure for producing images within the body of a subject. During an MRI scan, Radio Frequency (RF) pulses generated by a transmitter coil cause perturbations to the local magnetic field, and RF signals emitted by the nuclear spins are detected by a receiver coil. These RF signals are used to construct the MRI images.

Rapidly acquiring magnetic resonance images has been successfully used to guide various modalities of radiation therapy. U.S. Pat. No. 6,198,957 describes a therapeutic apparatus which combines a linear accelerator with MRI.

SUMMARY OF THE INVENTION

The invention provides for a method of correcting a magnetic field medical apparatus and a medical apparatus in the independent claims. Embodiments are given in the dependent claims.

In MR radiotherapy, the radiation source rotating around the MR magnet on a gantry contains ferromagnetic materials which can disturb the magnetic field within the imaging volume. This invention provides various different methods to eliminate or reduce these field perturbations: One method is based on a zero-crossing of the B0 magnetic field, so that the ferromagnetic disturbing element or ferromagnetic element can be placed in a way that its net magnetization is zero. The other two methods employ compensation elements, either passive (a ferromagnetic body with opposite magnetization) or active (a magnetic field coil).

These compensation methods may have the benefit that they are independent of the position and velocity of the gantry, since the B0 magnetic field has rotational symmetry and the compensation devices (if any) may be fixed to the rotating disturbing elements.

A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example a data may be retrieved over a modem, over the internet, or over a local area network.

'Computer memory' or 'memory' is an example of a computer-readable storage medium. Computer memory is any memory which is directly accessible to a processor. Examples of computer memory include, but are not limited to: RAM memory, registers, and register files.

'Computer storage' or 'storage' is an example of a computer-readable storage medium. Computer storage is any non-volatile computer-readable storage medium. Examples of computer storage include, but are not limited to: a hard disk drive, a USB thumb drive, a floppy drive, a smart card, a DVD, a CD-ROM, and a solid state hard drive. In some embodiments computer storage may also be computer memory or vice versa.

A 'processor' as used herein encompasses an electronic component which is able to execute a program or machine executable instruction. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. Many programs have their instructions performed by multiple processors that may be within the same computing device or which may even be distributed across multiple computing devices.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, gear sticks, steering wheel, pedals, wired glove, dance pad, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bistable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

Magnetic Resonance (MR) data is defined herein as being the recorded measurements of radio frequency signals emitted by atomic spins by the antenna of a Magnetic resonance apparatus during a magnetic resonance imaging scan. A Magnetic Resonance Imaging (MRI) image is defined herein as being the reconstructed two or three dimensional visualization of anatomic data contained within the magnetic resonance imaging data. This visualization can be performed using a computer.

Medical image data as used herein encompasses data which is descriptive of anatomical structures of a subject. A magnetic resonance image is a type of medical image data.

In one aspect the invention provides for a method of correcting a magnetic field of a medical apparatus. Correcting a magnetic field may be interpreted as making the magnetic field more uniform or reducing the change in the magnetic field due to the movement of ferromagnetic objects about the magnetic field. Correcting a magnetic field may also be interpreted as reducing magnetic field perturbations due to a ferromagnetic element or object. The medical apparatus comprises a magnetic resonance imaging system for acquiring magnetic resonance data from an imaging zone. The magnetic resonance imaging system comprises a magnet for generating the magnetic field within the imaging zone. The magnet is further adapted for generating the magnetic field such that the magnetic field has a zero crossing outside of the imaging zone. A zero crossing as used herein is a point where the direction and notably the polarity of the magnetic field lines changes. The magnetic field in the zero crossing may be zero or have a value which is approaching zero. The magnetic field zero crossing may be below a predetermined value. The medical apparatus further comprises a gantry configured for rotating about the imaging zone. The gantry is configured to rotate about a rotational axis. A gantry as used herein encompasses an apparatus adapted for rotating an object or objects about a rotational axis in a circular path.

In some embodiments the magnetic field may also have an axis of symmetry. For instance the magnet may be a cylindrical type magnet which has an axis through the centre of the imaging zone. In some embodiments the rotational axis of the gantry is aligned with the axis of the magnet.

The medical apparatus further comprises a ferromagnetic component. The ferromagnetic component may for instance be a portion of a medical instrument or treatment device. The gantry is further configured or adapted to rotate the ferromagnetic component about the rotational axis. The aim of correcting the magnetic field is to reduce the change in the magnetic field and individual voxels of the imaging zone as the ferromagnetic component is rotated about the rotational axis.

The method comprises the step of installing a magnetic correcting element located on a radial path perpendicular to the rotational axis. The magnetic correcting element may be adapted to be rotated by the gantry as the ferromagnetic component is rotated. The radial path passes within a predetermined distance of the ferromagnetic component. The magnetic correcting element is positioned on the radial path such that the change in the magnetic field within the imaging zone due to the rotation of the ferromagnetic component about the rotational axis is reduced. For instance the ferromagnetic component may in some instances be represented as a dipole when located on one side of the zero crossing. In some embodiments the magnetic correcting element is placed on the opposite side of the zero crossing along the radial path. This has the effect of the dipole moment which represents the ferromagnetic component roughly cancelling the dipole moment of the magnetic correcting element. The method further comprises the step of repeatedly measuring the magnetic field within the imaging zone for at least one gantry rotational position. In some embodiments the magnetic field is measured at multiple gantry rotational positions.

The method further comprises the step of repeatedly determining the change in the magnetic field in the imaging zone due to the ferromagnetic component using the measured magnetic field. In some embodiments the change is determined in the magnetic field in the imaging zone due to the rotation of the ferromagnetic component about the rotational axis using the measured magnetic field. That is to say in some embodiments the gantry may be left in a single position and in other embodiments the gantry may be moved to multiple positions with the magnetic field being measured at each of those positions. In some embodiments the magnetic field may be measured before the ferromagnetic component is installed. In this case it may not necessarily be necessary to rotate the gantry to understand the change in the magnetic field. The method further comprises the step of repeatedly adjusting the position of the magnetic correcting element along the radial path if the change in the magnetic field is above a predetermined threshold to iteratively reduce the change in the magnetic field. This for instance may be achieved by adjusting the position and recording it and then using this data to iteratively approach the position which essentially reduces the change in the magnetic field or corrects the magnetic field.

This embodiment may be beneficial because it provides for a method of correcting for the magnetic field of the ferromagnetic component that is independent of the position and velocity of the gantry.

In another embodiment the change in the magnetic field in the imaging zone is determined due to the rotation of the ferromagnetic component about the rotational axis using the measured magnetic field. In this embodiment the magnetic field is measured within the imaging zone at multiple gantry rotational positions.

In another embodiment the method further comprises the step of repeatedly repositioning the ferromagnetic component along the radial path after measuring the magnetic field to iteratively reduce the change in the magnetic field in the imaging zone due to the rotation of the ferromagnetic component about the rotational axis. This embodiment is beneficial because changing the position of the ferromagnetic component along the radial path may also lead to a reduction in the change in the magnetic field due to the ferromagnetic component. For instance the position of the ferromagnetic component could be changed relative to the magnetic correcting element and also the ferromagnetic component may be positioned partially on either side of the zero crossing. In this case the dipole moment of one portion of the ferromagnetic component may cancel the dipole moment of the other portion of the ferromagnetic component.

In another embodiment the method further comprises the step of repeatedly repositioning the ferromagnetic component along the radial path after measuring the magnetic field to iteratively reduce the change in the magnetic field in the imaging zone due to the ferromagnetic component. This embodiment may have the advantage that moving the ferromagnetic component relative to the magnetic correcting element and/or the zero crossing may be able to reduce the change in the magnetic field due to the ferromagnetic component.

In another embodiment the position of the ferromagnetic component along the radial path is selected empirically. This may for instance be performed by keeping a record of the magnetic field measurements and using this to iteratively approach the position of the ferromagnetic component which reduces the change in the magnetic field.

In another embodiment the position of the ferromagnetic component along the radial path is selected or determined by analysis and simulation. This may for example be performed by modeling the magnet and the ferromagnetic component.

An exemplary method of performing this is:

1. Generate equivalent magnetic model for each magnetic component on gantry (location and strength of equivalent magnetic dipole). This can be done either by detailed magnetic modeling of the component (if all relevant details are know) or by magnetic characterization in a laboratory environment 2. Make a simulation model of the gantry, with the equivalent magnetic dipoles of the magnetic components at their proper locations 3. Compute the field map in the imaging volume of the combined set of magnetic sources 4. Add compensating measures (magnetic objects, coils, as per this invention) to the model and vary their strengths and positions until the model predicts a net field disturbance smaller than the required tolerance 5. Build everything as designed and make final corrections empirically.

In another embodiment the apparatus further comprises a power supply. The power supply may for instance supply direct current. The medical apparatus further comprises a coil configured to generate a compensating magnetic field when supplied with electrical current by the power supply. The method further comprises the step of repeatedly adjusting the electrical current supplied by the power supply to the coil after measuring the magnetic field within the imaging zone to reduce the change in the magnetic field within the imaging zone due to the ferromagnetic component. In some embodiments this may be performed to reduce the change in the magnetic field within the imaging zone due to rotation of the ferromagnetic component about the rotational axis. The coil may be placed in a variety of positions. It may for instance be placed around the ferromagnetic component and used to create a dipole field which may roughly or approximately cancel the dipole field of the ferromagnetic component. In other embodiments the coil may be placed on other positions along the radial path. The plurality and the strength of the current can be used such that the dipole field generated by the coil may roughly or approximately cancel the dipole field generated by the ferromagnetic component. This embodiment is advantageous because it allows for the correction of the magnetic field without mechanically placing objects.

In another embodiment the coil is positioned around the ferromagnetic component.

In another embodiment the coil is positioned within a predetermined distance from the radial path.

In another embodiment the magnetic field correcting element is a coil configured to generate a compensating magnetic field when supplied with electrical current by the power supply.

In another embodiment the magnetic field correcting element is a ferromagnetic element.

In another embodiment the magnetic field correcting element is a permanent magnet.

In another embodiment the method further comprises installing at least one additional magnetic correcting element and repeating the correcting method for the at least one additional magnetic correcting element. This embodiment is advantageous because the method may be repeated for any number of ferromagnetic components.

In another embodiment the magnetic field is measured using a magnetometer.

In another embodiment the magnetic field is measured using the magnetic resonance imaging system. For instance a phantom may be placed in the imaging zone or a portion of the imaging zone and the magnetic resonance imaging system itself may be used to measure the magnetic field homogeneity.

In another embodiment the placement of the magnetic correcting element along the radial path is determined empirically.

In another embodiment the placement of the magnetic correcting element along the radial path is determined by analysis and simulation.

In another embodiment the data acquired during the measurement of the magnetic field is stored. The method may further comprise the step of retrieving the stored data and using this to determine the change in the magnetic field due to a displacement of the magnetic correcting element along the radial path. This may be beneficial because magnets which are constructed similarly may produce a very similar magnetic field. Once a magnetic correcting element has been correctly placed along the radial path for one such magnet this data may be useful in more rapidly placing a similar magnetic correcting element in a different magnet.

In another aspect the invention provides for a medical apparatus comprising a magnetic resonance imaging system for acquiring magnetic resonance data from an imaging zone. The magnetic resonance imaging system comprises a magnet for generating a magnetic field within the imaging zone. The magnet is further adapted for generating the magnetic field such that the magnetic field has a zero crossing outside of the imaging zone. The medical apparatus further comprises a gantry configured for rotating about the imaging zone. The gantry is configured to rotate about a rotational axis. The medical apparatus further comprises a ferromagnetic component. The gantry is further configured or adapted to rotate the ferromagnetic component about the rotational axis. The medical apparatus may comprise more than one ferromagnetic component. The medical apparatus further comprises a magnetic correcting element located on the radial path perpendicular to the rotational axis. The radial path passes within a predetermined distance of the ferromagnetic component. The magnetic correcting element is positioned on the radial path such that the change in the magnetic field within the imaging zone due to the rotation of the ferromagnetic component about the rotational axis is reduced. In some embodiments the magnetic correcting element is positioned on the radial path such that the change in the magnetic field within the imaging zone due to the ferromagnetic component is reduced. The advantages of this embodiment have been previously described.

In another embodiment the ferromagnetic component is positioned on the radial path to reduce the change in the magnetic field within the imaging zone due to the ferromagnetic component.

In another embodiment the ferromagnetic component is positioned on the radial path to reduce the change in the magnetic field within the imaging zone due to rotation of the ferromagnetic component about the rotational axis.

In another embodiment the apparatus further comprises a power supply. The medical apparatus further comprises a coil configured to generate a compensating magnetic field when supplied with electrical current by the power supply. The coil may generate a compensating magnetic field that compensates the dipole field generated by the ferromagnetic component. The compensating magnetic field is configured to reduce the change in the magnetic field within the imaging zone due to rotation of the ferromagnetic component about the rotational axis. The advantages of this embodiment have been previously discussed.

In another embodiment the apparatus further comprises a power supply. The medical apparatus further comprises a coil configured to generate a compensating magnetic field when supplied with electrical current by the power supply. The compensating magnetic field is configured to reduce the change in the magnetic field within the imaging zone due to the ferromagnetic component. The advantages of this embodiment have been previously discussed.

In another embodiment the coil is positioned around the ferromagnetic component.

In another embodiment the coil is positioned within a predetermined distance from that radial path.

In another embodiment the ferromagnetic component is a component of a radiotherapy apparatus.

In another embodiment the ferromagnetic component is a component of a linear accelerator or LINAC.

In another embodiment the ferromagnetic component is a component of a charged particle beam delivery system. A charged particle beam delivery system as used herein is a system which is adapted or constructed for shooting a beam of charged particles at a target.

In another embodiment the ferromagnetic component is a component of a charged particle optics.

In another embodiment the ferromagnetic component is a component of a bending magnet.

In another embodiment the ferromagnetic component is a component of a focusing magnet.

In another embodiment the ferromagnetic component is a collimator.

In another embodiment the ferromagnetic component is a component of a collimator.

In another embodiment the ferromagnetic component is a component of a shutter.

In another embodiment the ferromagnetic component is a component of an attenuator.

In another embodiment the ferromagnetic component is a component of a cooling system.

In another embodiment the ferromagnetic component is a component of a power supply.

In another embodiment the ferromagnetic component is a component of control hardware such as a controller.

In another embodiment the ferromagnetic component is a component of a beam dump.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
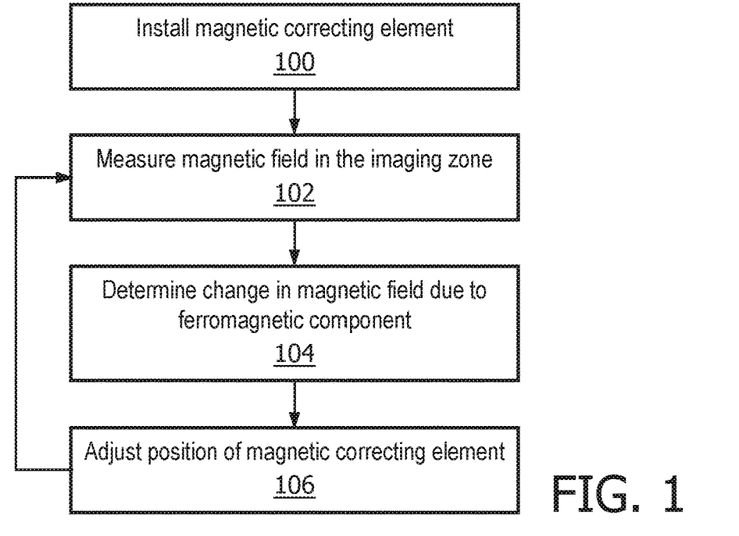
FIG. 1 shows a flow diagram which illustrates a method according to an embodiment of the invention.

FIG. 1 shows a flow diagram which illustrates a method according to an embodiment of the invention. In step 100 a magnetic correcting element is installed such that the magnetic correcting element is located on a radial path perpendicular to the rotational axis. In actual practice the magnetic correcting element may be located a short distance or a predetermined distance from the radial path. Next in step 102 the magnetic field in the imaging zone is measured to determine the effect of the ferromagnetic component and the magnetic correcting element on the magnetic field. In step 104 the change in the magnetic field due to the ferromagnetic component is determined. In step 104 the effectiveness of the magnetic correcting element for correcting for the dipole field of the ferromagnetic component is assessed. Next in step 106 the position of the magnetic correcting element along the radial path is adjusted. Steps 102, 104 and 106 are repeated iteratively to reduce the change in the magnetic field due to the ferromagnetic component. When the change in the magnetic field due to the ferromagnetic component is reduced to an acceptable or predetermined level then the method ends. This method may be extended by installing an additional or additional ferromagnetic components. For each ferromagnetic component added an additional magnetic correcting element may also be added. The method shown in FIG. 1 may then be repeated for each ferromagnetic component as it is installed into the medical apparatus.

Figure 2:
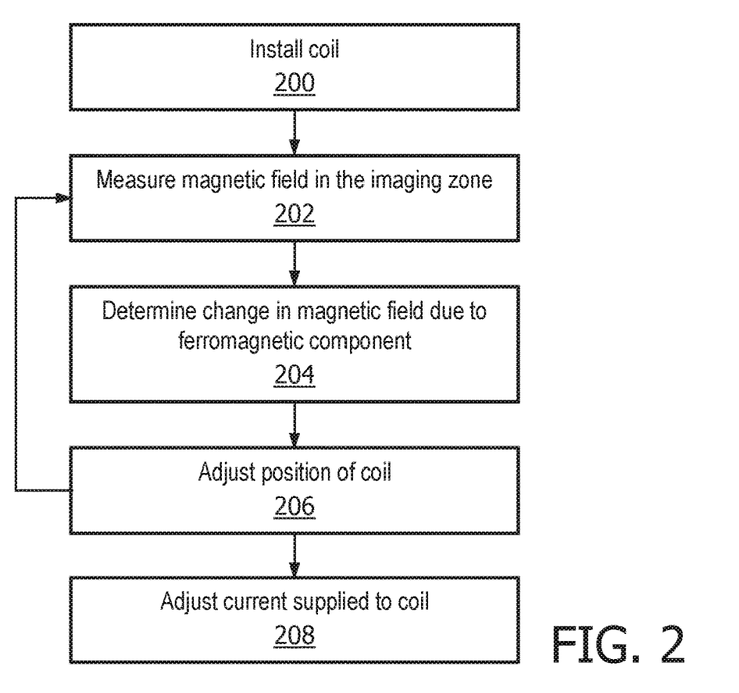
FIG. 2 shows a flow diagram which illustrates a method according to a further embodiment of the invention.

FIG. 2 shows a flow diagram which illustrates a further method according to an embodiment of the invention. In step 200 a coil is installed. Next in step 202 the magnetic field in the imaging zone is measured. In step 204 the change in the magnetic field due to the ferromagnetic component is determined. In step 206 the position of the coil relative to the radial path is optionally adjusted. In step 208 the current supplied to the coil is optionally adjusted. Steps 206 and 208 allow the correction of the magnetic field to be performed in multiple ways which allow fine correction of the magnetic field.

Figure 3:
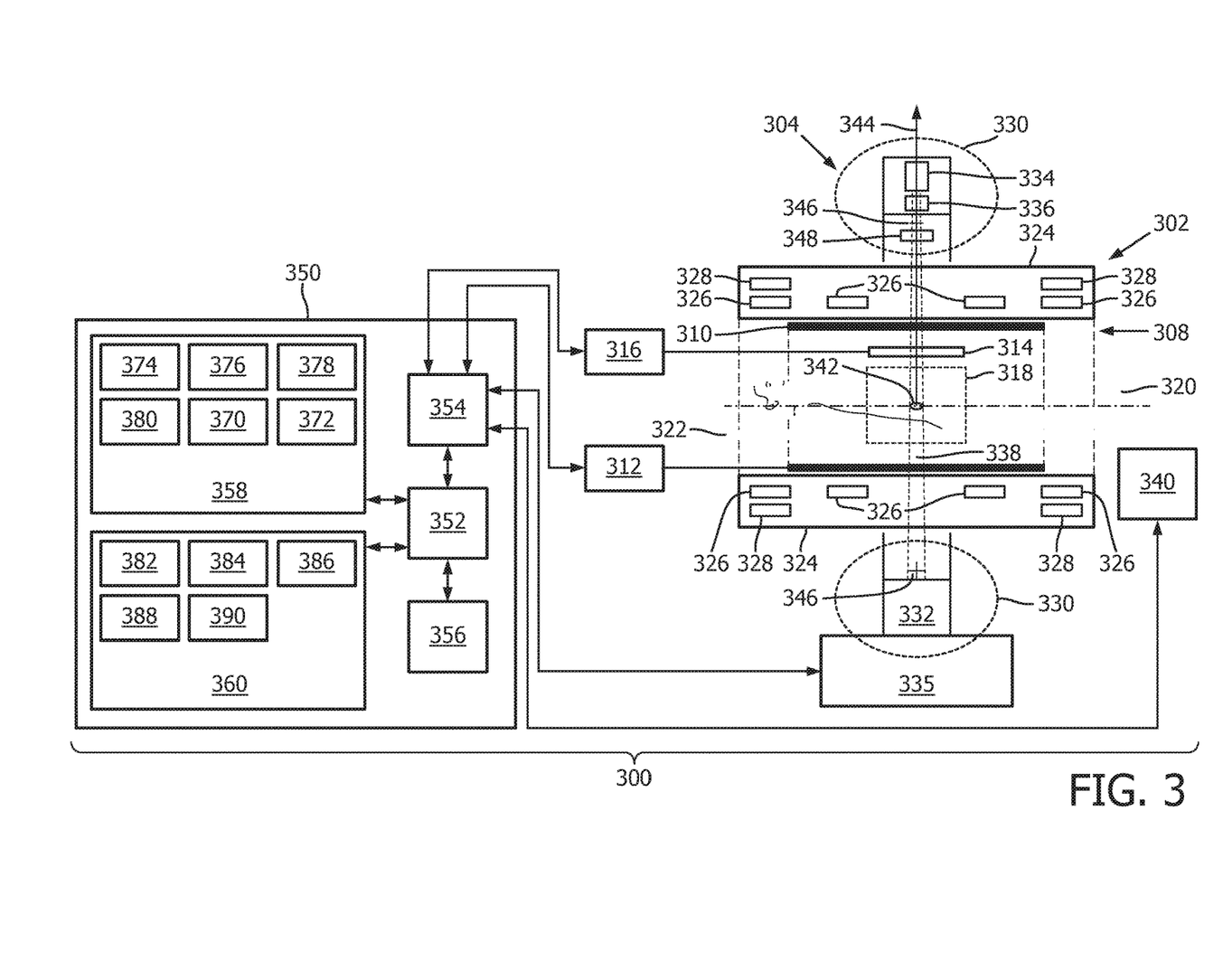
FIG. 3 illustrates a medical apparatus according to an embodiment of the invention.

FIG. 3 illustrates a medical apparatus according to an embodiment of the invention. The medical apparatus comprises a magnetic resonance imaging system 302. The magnetic resonance imaging system comprises a magnet 306. The magnet shown in FIG. 3 is a cylindrical type superconducting magnet. The magnet has a liquid helium cooled cryostat with superconducting coils. It is also possible to use permanent or resistive magnets. The use of different types of magnets is also possible for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils. Within the bore 308 of the cylindrical magnet 306 there is an imaging zone 318 where the magnetic field is strong and uniform enough to perform magnetic resonance imaging.

Within the bore 308 of the magnet there is also a magnetic field gradient coil 310 which is used to spatially encode magnetic spins within an imaging zone of the magnet during the acquisition of magnetic resonance data. The magnetic field gradient coil 310 is connected to a magnetic field gradient coil power supply 312. The magnetic field gradient coil is intended to be representative. Typically magnetic field gradient coils contain three separate sets of coils for spatially encoding in three orthogonal spatial directions. A magnetic field gradient power supply supplies current to the magnetic field gradient coils. The current supplied to the magnetic field coils is controlled as a function of time and may be ramped or pulsed.

Adjacent to the imaging zone 318 is a radio-frequency coil 314 which is connected to transceiver 316. Also within the bore 308 is a subject 320 reposing on a subject support 322. The radio-frequency coil 314 is adapted for manipulating the orientations of magnetic spins within the imaging zone and for receiving radio transmissions from spins also within the imaging zone. The radio-frequency coil 314 may contain multiple coil elements. The radio-frequency coil may also be referred to as a channel or an antenna. The radio-frequency coil 314 and radio frequency transceiver 316 may be replaced by separate transmit and receive coils and a separate transmitter and receiver. It is understood that the radio-frequency coil 314 and the radio frequency transceiver 316 are representative. The radio-frequency coil 314 may also represent a dedicated transmit antenna and a dedicated receive antenna. Likewise the transceiver may also represent separate transmitters and receivers.

The medical apparatus shown in FIG. 3 includes a radiation therapy system 304. The magnet 306 is a superconducting magnet and includes a cryostat 324 with several superconducting coils 326. There is also a compensation coil 328 which creates an area of reduced magnetic field 330 which surrounds the magnet 306. The radiation therapy system 304 in this embodiment is intended to be representative of radiation therapy systems in general. The components shown here are typical for LINAC and x-ray therapy systems. However with minor modifications such as using a split magnet charged particles or beta particle radiation therapy systems can also be illustrated using this diagram. There is a gantry 332 which is used to rotate a radiotherapy source 334 about the magnet 306. The gantry 332 is rotated about the axis of rotation 333 by a rotation actuator 335. There is a radiation therapy source 334 which is rotated by the gantry 332. The radiotherapy source 334 generates a radiation beam 338 which passes through collimator 336. In the Fig. a target zone labeled 342 which is irradiated by the radiation beam 338 is shown. As the radiation source 334 rotates about the axis of rotation 333 the target zone 342 is always irradiated. There is also a support positioning system 340 for positioning the support 322 to optimize the location of the target zone 342 relative to the radiation therapy system 304.

A radial path 344 which is perpendicular to the axis of rotation 333 is shown as passing through the ferromagnetic component 336 or collimator. The zero crossing 346 is shown as being located on the radial path 344. The ferromagnetic component 336 is on one side of the zero crossing 346 and the magnetic correcting element 348 is located on the other side of the zero crossing 346. The magnetic correcting element 348 is shown as being located on the radial path 344.

The medical apparatus 300 is further shown as comprising a computer system 350. The computer system comprises a processor 352, a hardware interface 354, a user interface 356, computer storage 358, and computer memory 360. The processor 352 is connected to and can operate with all of these components 354, 356, 358, 360. The hardware interface 354 is shown as being connected to the transceiver 316, the power supply 312, the rotation actuator 335, and the support positioning system 340. The hardware interface 354 allows the processor 352 to send and receive control signals to all of these components, 312, 316, 335, 340.

The computer storage 358 is shown as containing magnetic resonance data 370 that was acquired using the magnetic resonance imaging system 302. The computer storage 358 is further shown as containing the magnetic resonance image 372 that was reconstructed from the magnetic resonance data 370. The computer storage 358 is further shown as containing a treatment plan 374. The treatment plan contains instructions executable by the medical apparatus 300 which case the medical apparatus to treat the subject 320 using the radiotherapy source 334. The computer storage 358 is further shown as containing an image registration 376. The image registration allows the processor 352 to locate the target zone 342 within the subject 320. The computer storage 358 further contains at least one pulse sequence 378. The pulse sequences 378 may be used for acquiring data for guiding the radiotherapy source 334 and/or for acquiring magnetic field measurements from a phantom which is not shown in this diagram. The computer storage 358 is further shown as containing magnetic field measurements 380. The magnetic field measurements 380 may be used to iteratively select a position for the magnetic field correcting element 348.

The computer memory 360 is shown as containing computer executable code for controlling the operation and function of the medical apparatus 300. The computer storage is shown as containing a control module 382. The control module contains the instructions for operating and controlling the medical apparatus 300. The computer memory 360 is further shown as containing a command generation module 384. The command generation module 384 is adapted for using the treatment plan 374 and in some embodiments the image registration 376 to generate commands which cause the medical apparatus 300 to treat the target zone 342. The computer memory 360 is shown as further containing a magnetic resonance control module 386. The magnetic resonance control module 386 is adapted for generating commands and controlling the operation of the magnetic resonance imaging system 302 using a pulse sequence 378. The computer memory 360 is further shown as containing an image reconstruction module 388. The image reconstruction module 388 contains computer executable code for reconstructing the magnetic resonance image 372 from the magnetic resonance data 370. The computer memory 360 is further shown as containing an image segmentation module 390. The image segmentation module 390 contains computer executable code for segmenting the magnetic resonance image 372 and performing the image registration 376.

The embodiment shown in FIG. 3 is exemplary and other types of ferromagnetic components that could be rotated by the gantry. For instance the gantry could be rotating charged particle optics for a charged particle beam system. In such embodiments the cylindrical magnet could be replaced with a split magnet design which allows the charged particle beam to pass freely to the subject.

Figure 4:
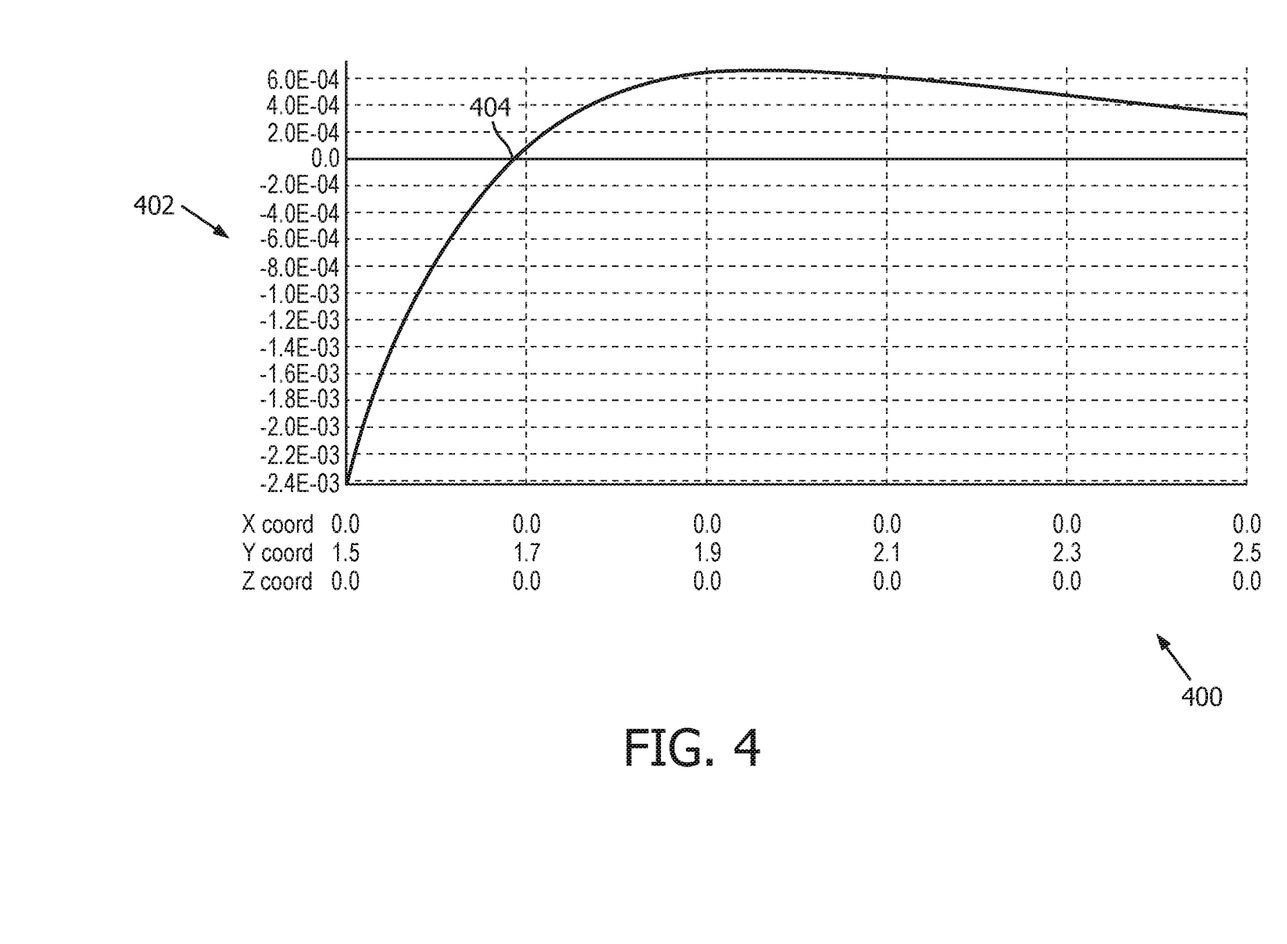
FIG. 4 plots calculated magnetic field values for a magnet according to an embodiment of the invention.

FIG. 4 shows the radial field distribution of a magnet of a magnetic resonance imaging system. The magnet is a cylindrical type magnet. In FIG. 4 the Bz component in the z=0 plane is shown. The x-axis 400 gives the x, y and z coordinates in meters. The y-axis 402 gives the magnetic flux density in Tesla. The point labeled 404 is the point where the magnetic field strength goes to 0 and is the zero crossing.

Figure 5:
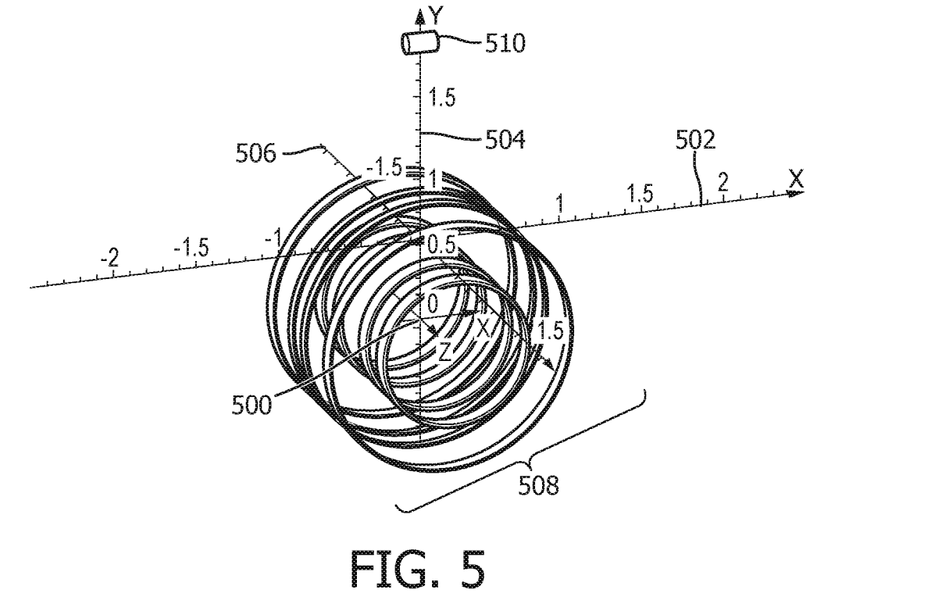
FIG. 5 illustrates a ferromagnetic component adjacent to a magnet.

FIG. 5 illustrates a ferromagnetic component 510 placed adjacent to a magnet. There is an origin of a coordinate system 500 shown. The imaging zone is located in the vicinity of the origin of the coordinate system 500. The x-coordinate is labeled 502, the y-coordinate system is labeled 504 and the z-coordinate system is labeled 506. The z-coordinate and x-coordinate are offset from the origin 500. The y-axis may be considered to be a radial path along with the ferromagnetic component is moved. There is the ferromagnetic component 510 shown relative to the placement of the superconducting magnet coils 508. The magnet coils 508 are intended to represent the magnet used to generate the magnetic field shown in FIG. 4.

Figure 6:
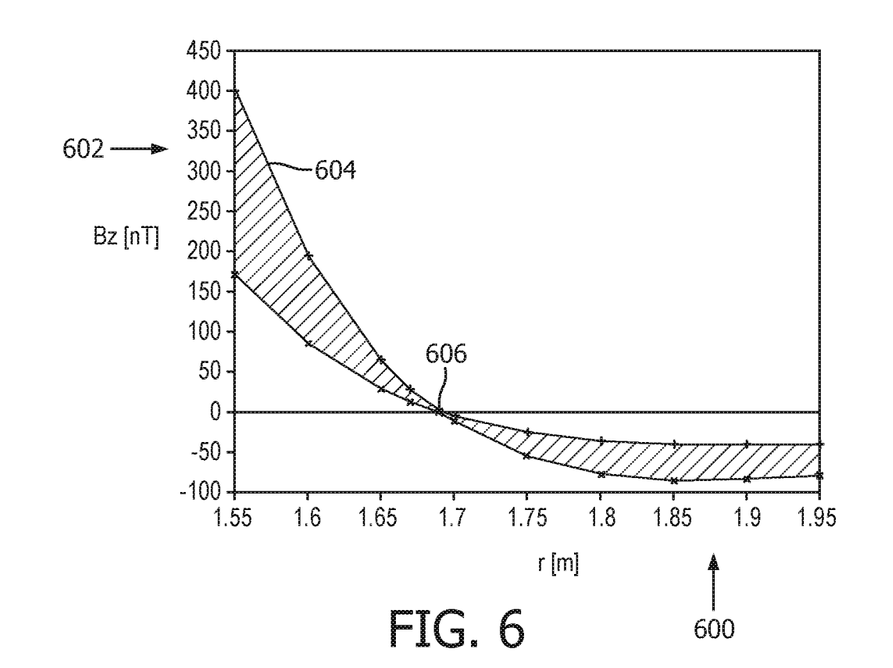
FIG. 6 plots the effect of the ferromagnetic component on the magnetic field in the imaging zone as a function of position.

FIG. 6 illustrates how the ferromagnetic component 510 of FIG. 5 can be positioned to reduce the effect of it on the magnetic field in the imaging zone. In this graph the radial distance in meters is the x-axis and is labeled 600. The y-axis 602 shows the Bz component of the magnetic field in nanoTesla. The curved or shaded region labeled 604 shows the range of the magnetic field contribution due to the ferromagnetic component 510 when placed at a particular radial distance. The ferromagnetic component will affect different portions of the imaging zone differently. In this Fig. it can be seen that as the ferromagnetic component 510 is moved to the zero crossing 606, the effect of the ferromagnetic component 510 on the magnetic field goes to 0. This Fig. illustrates how positioning a ferromagnetic component 510 relative to the zero crossing can be used to reduce the effect of the ferromagnetic component 510 on the magnetic field within the imaging zone.

Figure 7:
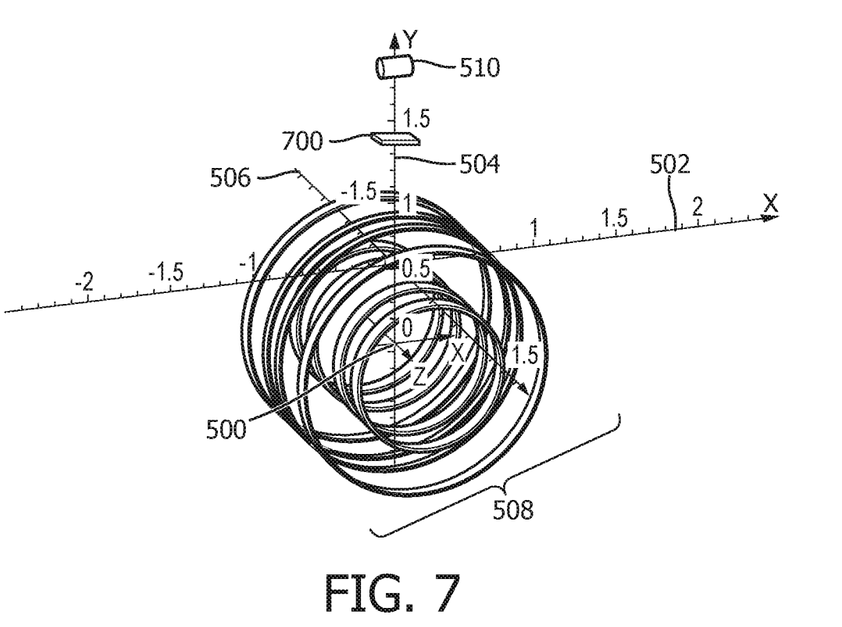
FIG. 7 illustrates a ferromagnetic component and a magnetic correcting element adjacent to a magnet.

FIG. 7 shows an arrangement similar to that shown in FIG. 5. However, in this example an iron block 700 is used as a magnetic correcting element.

Figure 8:
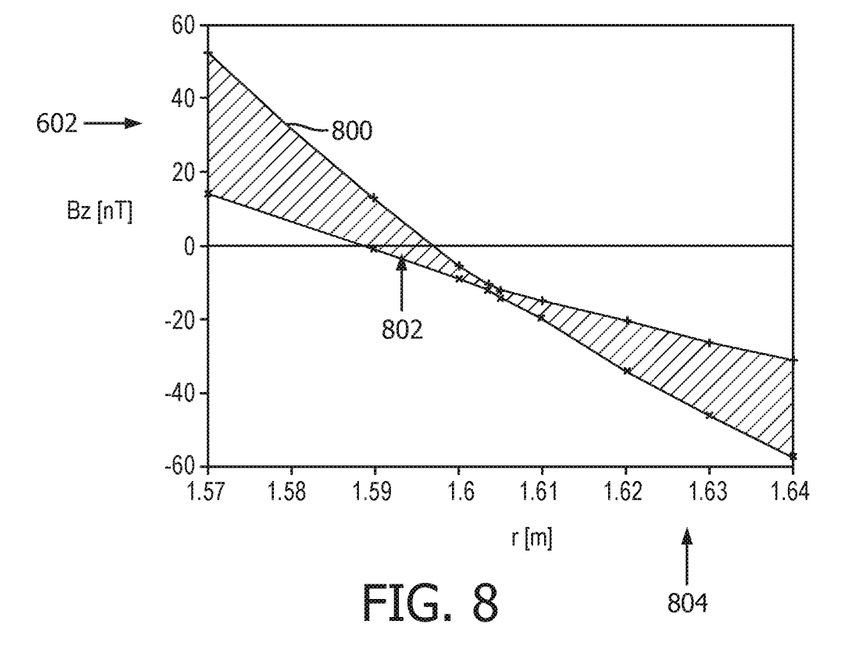
FIG. 8 plots the effect of the ferromagnetic component and the magnetic correcting element on the magnetic field in the imaging zone as a function of position of the magnetic correcting element.

FIG. 8 is similar to that shown in FIG. 6. Instead of showing the effect of the range of the magnetic field contribution 800 due to the changing position of the ferromagnetic component 510 the iron block 700 is moved into different positions. The x-axis 804 shows the position of the correcting element or iron block 700. The curve labeled 800 shows the range of magnetic field contribution due to the ferromagnetic component 510 and the iron block. It can be seen that when the ferromagnetic component 700 is moved approximately into position 802 that the effect of the ferromagnetic component 510 and the iron block 700 on the magnetic field in the imaging zone is minimized.

Figure 9:
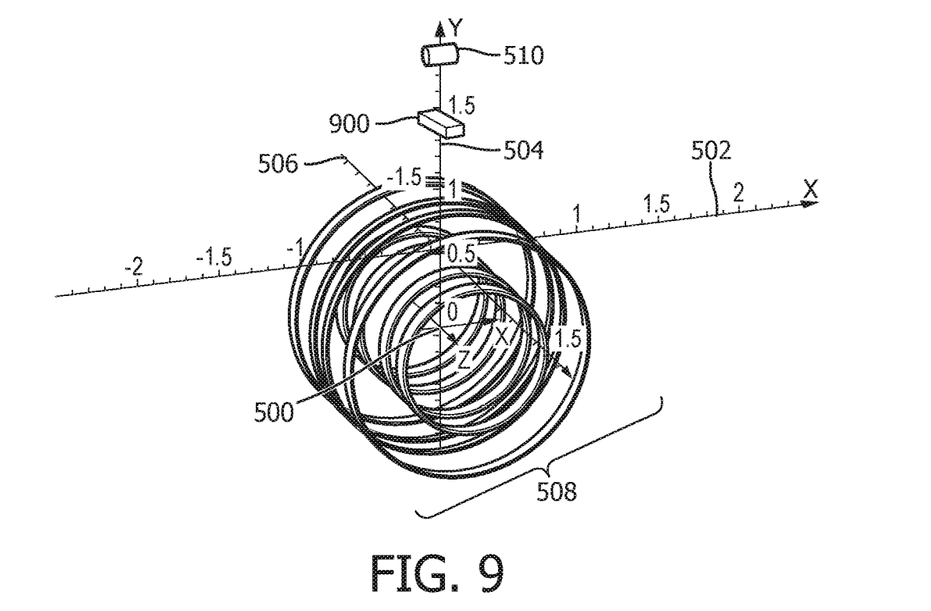
FIG. 9 illustrates a ferromagnetic component and a permanent magnet adjacent to a magnet.

FIG. 9 is similar to the FIGS. 5 and 7 but an alternate embodiment is shown. In this embodiment a permanent magnet 900 is located on the y-axis. The permanent magnet 900 may be moved to different positions and may be used to cancel or at least partially cancel the change in the magnetic field in the imaging zone due to the ferromagnetic component 510.

FIG. 10 is again similar to FIGS. 5, 7 and 9 but shows an alternative embodiment. In the embodiment shown in FIG. 10 a coil 1000 is surrounding the ferromagnetic component 510. The coil 1000 is connected to a direct current power supply and is used to generate a dipole field which approximately cancels the dipole field of the ferromagnetic component 510.

Figure 10:
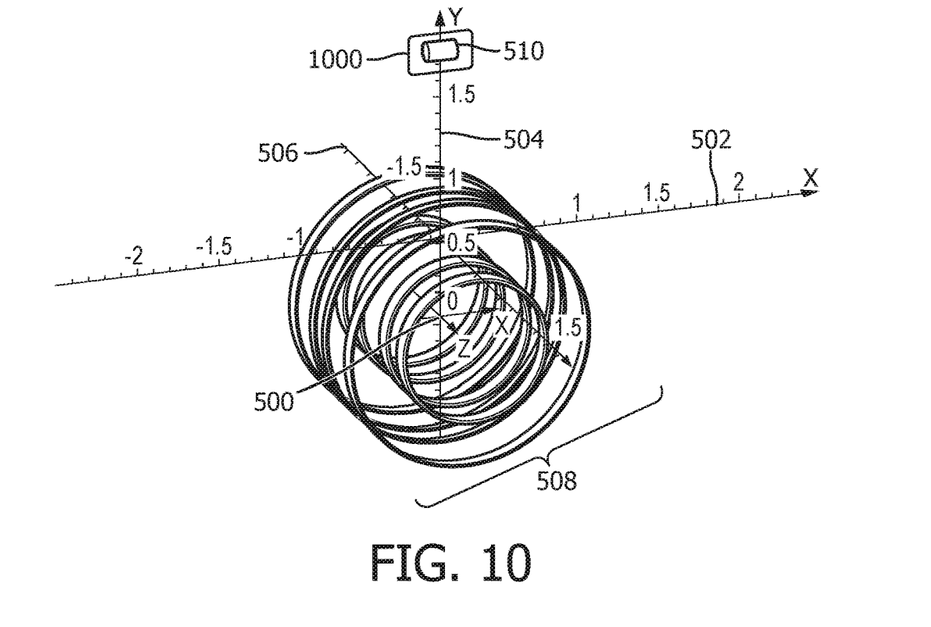
FIG. 10 illustrates a ferromagnetic component and a compensating coil adjacent to a magnet.
Figure 11:
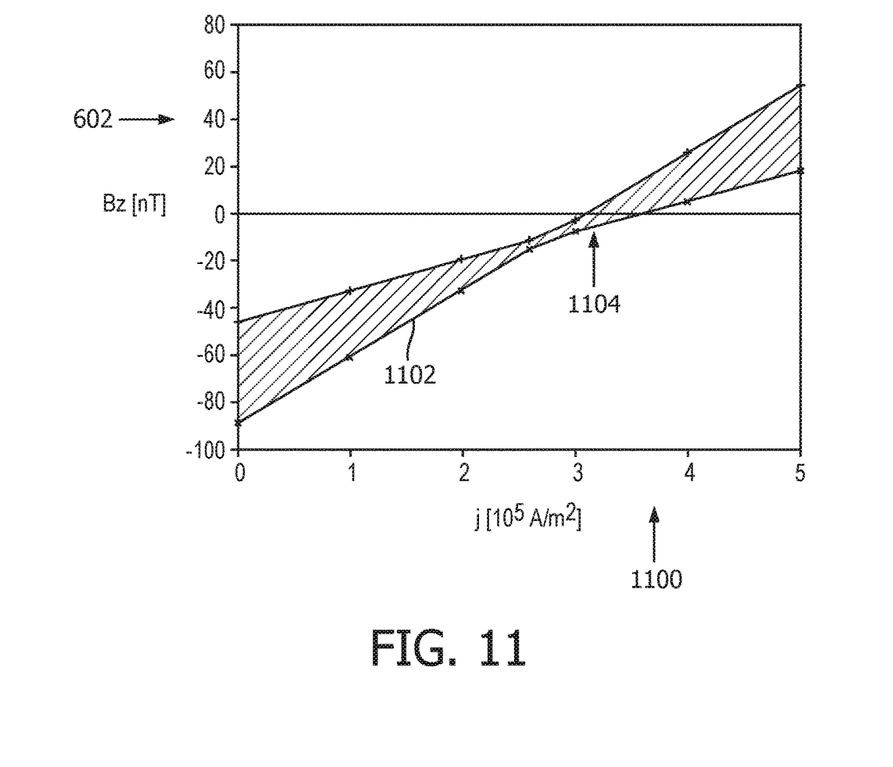
FIG. 11 plots the effect of the ferromagnetic component and the coil on the magnetic field in the imaging zone as a function current supplied to the coil.

FIG. 11 shows the effectiveness of the embodiment shown in FIG. 10. In the plot shown in FIG. 11 the x-axis 1100 is the current supplied to the coil. The y-axis is the magnetic field strength 602 in nanoTeslas. The curve 1102 shows the range of contribution in the magnetic field due to the ferromagnetic component and the energized coil 1100. It can be seen that when the current is set to the value at 1104 or to approximately this value that the effect of the ferromagnetic component 510 on the imaging zone is minimized.

Figure 12:
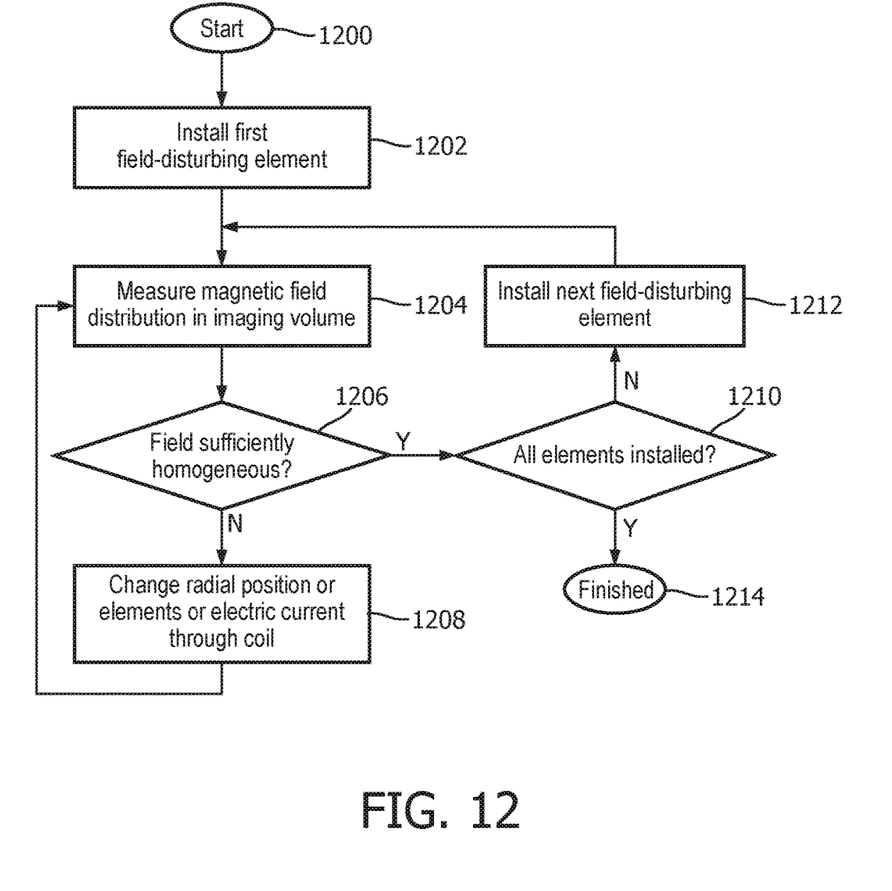
FIG. 12 shows a flow diagram which illustrates a method according to a further embodiment of the invention.

FIG. 12 shows a flowchart which illustrates a further embodiment of a method according to the invention. In step 1200 the method starts. Next in step 1202 a first field-disturbing element is installed into the medical apparatus. The field-disturbing element is equivalent to a ferromagnetic element. Next in step 1204 the magnetic field distribution is measured in the imaging volume or the imagining zone. Next in step 1206 is a decision box and the magnetic field measurements are compared to a predetermined criteria to determine if they are sufficiently homogeneous or not. If they are not sufficiently homogeneous then box 1208 is performed. In box 1208 the radial position of the ferromagnetic component or of a magnetic correcting element or a coil is changed. Alternatively the current through a coil may also be changed. After block 1208 is performed block 1204 is performed again. In block 1204 again the magnetic field distribution is measured in the imaging volume. This loop is repeated iteratively until the field is determined sufficiently homogeneous in block 1206. When it is determined sufficiently homogeneous decision block 1210 is then performed. In this block it is determined if all elements, that is to say all field-disturbing elements or ferromagnetic elements, have been installed. If this is not the case then block 1212 is performed next. In block 1212 the next field-disturbing element or ferromagnetic element is installed into the system. After the next field-disturbing element is installed the steps of 1204, 1206 and 1208 are repeated until the field is sufficiently homogeneous again. Then block 1210 is repeated. In block 1210 if all elements have been installed, then the method finishes in block 1214.

The medical apparatus may require a radiation source as well as some electronic equipment to be attached to a rotating gantry around the MR magnet. The technical challenge is to minimize interference between the two parts of the system (i.e. the radiation source and the MRI magnet) while still maintaining the highest possible precision of both imaging and radiation dose delivery.

One the one hand, the magnetic field produced by the Magnetic Resonance (MR) magnet is preferably as small as possible within the toroidal region where the linear accelerator is moved around. On the other hand, the radiation source preferably does not influence the magnetic field in the imaging region, independent of the position or velocity of the gantry. Embodiments of the invention may address the latter aspect by providing methods to compensate the field perturbations of the moving elements.

In combined MR radiotherapy, MR images may be taken during the radiation treatment, while the radiation source is rotating around the MR magnet. Several components containing ferromagnetic material (e.g. linear accelerator, power supply) may therefore be fixed to a rotating gantry within the MR main magnetic field. Due to their magnetization, these objects perturb the stationary homogeneous magnetic field in the imaging region, potentially leading to image artifacts and distortion. Since the disturbing objects are rotating, the field perturbations are time-dependent. The amount of ferromagnetic material in a linear accelerator used for MR radiotherapy can lead to variations of the Bz field component in the imaging volume much greater than 50 nT, which may decrease image quality.

While small static perturbations can be compensated to a certain extent by static shimming or software-based image manipulation, these techniques are not suited for time-dependent perturbations caused by an object on a rotating gantry.

The present invention offers a means of compensating these perturbations in a way that the magnetic field is again sufficiently homogeneous within the imaging volume, even under non-static conditions.

The invention may consist of three different solutions of the problem, employing:

1) a specially shaped B0 magnetic field featuring a zero crossing with dedicated positioning of the disturbing object(s) relative to the field zero crossing,
2) a specially shaped B0 magnetic field featuring a zero crossing and one ferromagnetic compensation element for each disturbing object,
3) an active compensation coil around the disturbing object The MR radiotherapy system may consist of a limited number of discrete magnetic objects (e.g. transformer core, magnetron magnet, microwave circulator) for each of which the magnetic dipole moment is compensated locally and independently.

In the following, three methods for field compensation are presented. The disturbing object in all example calculations is a solid iron cylinder with L=200 mm and r=63.6 mm (weight 20 kg). This corresponds approximately to the amount of iron inside a linear accelerator for MR radiotherapy. The cylinder axis is placed in the z=0 plane tangential to the gantry ring.

The calculations presented in FIGS. 4, 6, 8, and 11 were performed with a finite elements simulation software using a realistic 1.5 T split-coil magnet design which exhibits a zero-crossing of the Bz field component at r=1.68 m in the z=0 plane. The radial field distribution of the unperturbed magnet is plotted in FIG. 4. All three methods described in the following can be used with such a magnet design, while the third method is also possible without a Bz zero-crossing.

All plots (FIGS. 5, 7, and 11) of the residual magnetic field variations refer to minimum and maximum field values within a spherical imaging volume of radius 0.25 m.

1) The first method makes use of a zero crossing in the main magnetic field at the position of the disturbing ferromagnetic element and is illustrated in FIGS. 5 and 6. This field configuration may have the advantage that ferromagnetic components placed on different sides of the field zero crossing are magnetized in opposite directions, so that their contributions to the field in the imaging volume cancel and the net magnetic dipole moment is zero. The quality of field cancellation in the entire imaging volume depends on the exact magnet design and geometry of the ferromagnetic components.

In this first example there is only one ferromagnetic body (cylinder 10) which can be displaced radially. The effect of the body on the homogeneity of the imaging field is shown in FIG. 5 as a function of the radial position of the cylinder. In this example, placing the cylinder at around r=1.68 m when positioned in a way that part of the body is on one side of the zero crossing and part of the body is on the other side, leads to a good cancellation and a residual field perturbation of well below 50 nT.

2) The second method can be employed when the position of the disturbing body is fixed and cannot be chosen to be at the point of the Bz zero crossing and is illustrated in FIGS. 7 and 8. In this case a second ferromagnetic component on the opposite side of the zero crossing is used to cancel the effect of the first one. By varying the radial position of this compensation element, the net dipole moment can again be chosen to be zero. The remaining higher multipole orders of the magnetic field decrease at least as $1/r^5$, so that their effect within the imaging volume is negligible. To demonstrate that this method is rather insensitive to the exact shape of the bodies, the compensation element for the cylindrical disturbing body in this example is a rectangular block of arbitrarily chosen dimensions 200 mm×120 mm×30 mm (see FIG. 7). For a fixed position of the cylinder at r=1.85 m the optimum position of the block is found to be at r=1.603 m. The variation of the field in the imaging region caused by the ferromagnetic components is shown in FIG. 8 as a function of the radial position of the compensation block. As can be seen in the plot, the variations of the field in the imaging region can easily be made much smaller than 50 nT. Alternatively, the ferromagnetic compensation block can be replaced by a permanent magnet as shown in FIG. 9. Choosing the correct radial position of the permanent magnet leads to similarly low residual fields in the imaging volume, while the exact shape of the permanent magnet is of minor importance. Using a permanent magnet, this scheme is suitable for B0 magnets with and without a zero crossing of the magnetic field.

3) The third method is based on active compensation of the effect of a ferromagnetic component by means of an electric current in a coil enclosing the object. This is illustrated in FIGS. 10 and 11. By varying the electric current, the optimum compensation can be found. This method can also be employed when there is no zero crossing of the main magnetic field available, as the direction of the compensation field depends only on the direction of the electric current. FIG. 10 shows an example geometry with a conductor 1000 (cross section 10 mm×10 mm, rectangular area 400 mm×200 mm) or coil enclosing the disturbing cylinder 510. A calculation of the residual field contribution of the cylinder and coil system on the magnetic field in the imaging region is plotted in FIG. 11. In this configuration, a current density of $3\times10^5$ Am$^{-2}$ (which can easily be achieved in a real system) leads to a reduction of the field perturbation to well below 50 nT.

When the magnetic field in the gantry region is not rotationally symmetric (i.e. when static field perturbations by other objects close to the MR scanner have a relevant influence), the magnetization of rotating objects will depend on the rotation angle. In this case, compensation of the rotating magnetic object can still be achieved in one of the following two ways:

a) Static field perturbations can be compensated by static compensation elements in the same way as the rotating objects described above. This procedure must take place before the elements on the gantry are mounted.

b) When a compensation coil is used (method 3 above), the current can be made angle-dependent to account for the angle-dependent magnetization. In this case the installation procedure described below must be repeated at a number of different angles to determine a function $I(\varphi)$ for the compensation current I at angular position $\varphi$.

The invention may be applied for any configuration of MR magnets where ferromagnetic elements in the outer region of the main magnetic field disturb the field homogeneity in the imaging region. Embodiments of the invention may be useful when the disturbing element(s) are not static (as is the case for a rotating gantry).

The following method may be used for installing and calibrating the system: The disturbing objects should be installed and compensated one after the other. Once a disturbing object is sufficiently well calibrated, the next element can be installed and so on. The calibration sequence for each of the elements is an iterative procedure, consisting of alternate field measurement and recalibration steps. The field measurement is performed in the same way as in shimming of a conventional MRI magnet, where several test measurements on a spherical surface are taken. The calibration step depends on the field compensation method chosen:

Method 1: The disturbing element is displaced radially.

Method 2: The compensation element is displaced radially.

Method 3: The electric current through the compensation coil is varied.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A medical apparatus comprising:
a bore-type magnetic resonance imaging system including a cylindrical magnet including first coils configured to generate a $B_0$ field in an imaging region;
a ferromagnetic component located adjacent and outside of the cylindrical magnet, the ferromagnetic component causing changes in the $B_0$ field in the imaging region;
a magnetic field correcting element disposed outside of the cylindrical magnet adjacent the ferromagnetic component, the magnetic field correcting element being positioned and configured to offset the changes in the $B_0$ field caused by the ferromagnetic component; and
a gantry configured to rotate the ferromagnetic component and the magnetic field correcting element concurrently around an outside of the cylindrical magnet and the imaging region.

2. The medical apparatus of claim 1, wherein the magnetic field correcting element is a coil configured to generate a compensating magnetic field when supplied with electrical current by a power supply.

3. The medical apparatus of claim 1, wherein the magnetic field correcting element is a ferromagnetic element.

4. The medical apparatus of claim 1, wherein the magnetic field correcting element is a permanent magnet.

5. The medical apparatus of claim 1, wherein the magnetic field correcting element is located on a radial path perpendicular to a rotational axis of the ferromagnetic component.

6. The medical apparatus of claim 1, wherein the magnetic field correcting element is located a predetermined distance from a radial path perpendicular to a rotational axis of the ferromagnetic component.

7. The medical apparatus of claim 1, wherein the gantry is configured to rotate the magnetic field correcting element about a rotational axis with the ferromagnetic component.

8. The medical apparatus of claim 1, further including one or more additional magnetic field correcting elements disposed outside of the cylindrical magnet adjacent the ferromagnetic component.

9. The medical apparatus of claim 8, wherein the one or more additional magnetic field correcting elements includes a coil configured to generate a compensating magnetic field when supplied with electrical current by a power supply.

10. The medical apparatus of claim 8, wherein the one or more additional magnetic field correcting elements includes a ferromagnetic element.

11. The medical apparatus of claim 8, wherein the one or more additional magnetic field correcting elements includes a permanent magnet.

12. The medical apparatus of claim 8, wherein the additional magnetic field correcting element is positioned and configured to offset the changes in the $B_0$ field caused by the ferromagnetic component.

13. The medical apparatus of claim 8, wherein the gantry is configured to rotate the one or more additional magnetic field correcting elements about the rotational axis with the ferromagnetic component.

14. A medical apparatus comprising:
a bore-type magnetic resonance imaging system including a cylindrical magnet including first coils configured to generate a $B_0$ field in an imaging region;
a ferromagnetic component located adjacent and outside of the cylindrical magnet, the ferromagnetic component causing changes in the $B_0$ field in the imaging region;
a plurality of magnetic field correcting elements disposed outside of the cylindrical magnet adjacent the ferromagnetic component, the plurality of magnetic field correcting elements being positioned and configured to offset the changes in the $B_0$ field caused by the ferromagnetic component; and
a gantry configured to rotate the ferromagnetic component and the plurality of magnetic field correcting elements concurrently around the cylindrical magnet and the imaging region.

15. The medical apparatus of claim 14, wherein the magnetic field correcting elements are ferromagnetic elements.

16. The medical apparatus of claim 14, wherein the magnetic field correcting elements are permanent magnets.

17. The medical apparatus of claim 14, wherein the magnetic field correcting elements are located on a radial path perpendicular to a rotational axis of the ferromagnetic component.

18. The medical apparatus of claim 14, wherein the plurality magnetic field correcting elements are located a predetermined distance from a radial path perpendicular to a rotational axis of the ferromagnetic component.

19. The medical apparatus of claim 14, wherein the gantry is configured to rotate the plurality of magnetic field correcting elements about a rotational axis with the ferromagnetic component.

* * * * *